(12) United States Patent
Peters et al.

(10) Patent No.: US 11,592,380 B2
(45) Date of Patent: Feb. 28, 2023

(54) SYSTEM AND METHOD FOR DETECTING A THICKNESS OF A LAYER

(71) Applicant: Robert Bosch GmbH, Stuttgart (DE)

(72) Inventors: Christian Peters, Sunnyvale, CA (US); Beatrix Mensch, Illertissen (DE); Thomas Rocznik, Mountain View, CA (US); Seow Yuen Yee, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 16/634,047

(22) PCT Filed: Dec. 17, 2018

(86) PCT No.: PCT/EP2018/085217
§ 371 (c)(1),
(2) Date: Jan. 24, 2020

(87) PCT Pub. No.: WO2019/129523
PCT Pub. Date: Jul. 4, 2019

(65) Prior Publication Data
US 2021/0148800 A1 May 20, 2021

Related U.S. Application Data

(60) Provisional application No. 62/610,401, filed on Dec. 26, 2017.

(51) Int. Cl.
*G01N 9/00* (2006.01)
*G01N 25/18* (2006.01)

(52) U.S. Cl.
CPC .............. *G01N 9/00* (2013.01); *G01N 25/18* (2013.01)

(58) Field of Classification Search
None
See application file for complete search history.

(56) References Cited

U.S. PATENT DOCUMENTS 6,381,488 B1 * 4/2002 Dickey ................. A61B 5/445
600/474
7,820,972 B2 * 10/2010 Miyamae ............ A61B 5/0059
250/341.8

(Continued)

FOREIGN PATENT DOCUMENTS

WO 2016/054348 A1 4/2016

OTHER PUBLICATIONS

Ametherm Circuit Protection Thermistors, Blog>>Thermal Time Constant and NTC Thermistors: A Practical Study copyright 1998-2013 Ametherm, Inc., downloaded from https://www.ametherm.com/blog/thermistors/thermal-time-constant-ntc-thermistors), on May 18, 2021 (Year: 2013).*

(Continued)

*Primary Examiner* — Eman A Alkafawi
*Assistant Examiner* — Denise R Karavias
(74) *Attorney, Agent, or Firm* — Maginot, Moore & Beck LLP

(57) ABSTRACT

A thickness analyzer unit for determining a thickness of a layer includes a temperature change device, a temperature sensor, a memory, and a controller. The temperature change device is configured to induce a temperature change of the layer from a first temperature value to a second temperature value. The temperature sensor is configured to generate first temperature data corresponding to the first temperature value and second temperature data corresponding to the second temperature value. The memory is configured to store the first and second temperature values, a thermal conductivity value, a specific thermal capacity value, and a density value. The controller is configured (i) to determine (Continued)

a time constant value of the layer based on the first and second temperature values, and (ii) to determine the thickness of the layer based on the time constant value, the thermal conductivity value, the specific thermal capacity value, and the density value.

14 Claims, 5 Drawing Sheets

(56) References Cited

U.S. PATENT DOCUMENTS

| | | | | |
|---|---|---|---|---|
| 2002/0031164 | A1* | 3/2002 | Scheidt | G01B 11/0658 374/7 |
| 2008/0097559 | A1* | 4/2008 | Eggers | A61B 18/1233 607/102 |
| 2011/0308548 | A1* | 12/2011 | Amundsen | G01B 21/085 374/7 |
| 2016/0331300 | A1* | 11/2016 | Shih | A61B 5/1075 |
| 2017/0347891 | A1* | 12/2017 | Rogers | A61B 5/01 |
| 2019/0183350 | A1* | 6/2019 | Bonmarin | A61B 5/445 |

OTHER PUBLICATIONS

Espacenet, machine translation, Schulz et al., WO9621857A1, Jul. 18, 1996 (Year: 1996).*

International Search Report corresponding to PCT Application No. PCT/EP2018/085217, dated Feb. 14, 2019 (3 pages).

Marz, Dr. Martin et al., Thermal Modeling of Power-electronic Systems, Thermal System Modeling, White Paper, Infineon Technologies AG, Munich, pp. 1-20, published at least as early as Dec. 25, 2017 (20 pages).

Niemann, Henrik et al., A Simple Method for Estimation of Parameters in First order Systems, Journal of Physics Conference Series 570 (2014) 012001, European Workshop on Advanced Control and Diagnosis, pp. 1-12 (12 pages).

Rowell, D., Review of First- and Second-Order System Response, Massachusetts Institute of Technology, Department of Mechanical Engineering, 2.151 Advanced System Dynamics and Control, pp. 1-41, Oct. 22, 2004 (41 pages).

* cited by examiner

SYSTEM AND METHOD FOR DETECTING A THICKNESS OF A LAYER

This application is a 35 U.S.C. § 371 National Stage Application of PCT/EP2018/085217, filed on Dec. 17, 2018, which claims the benefit of U.S. provisional application Ser. No. 62/610,401, filed on Dec. 26, 2017, the disclosures of which are herein incorporated by reference in their entirety.

FIELD

This disclosure relates to the field of heat transfer and, in particular, to sensing a thickness of a layer based on heat transfer.

BACKGROUND

Heat transfer is the study of the use, conversion, and exchange of thermal energy between physical systems. Heat transfer includes thermal conduction, thermal convection, and thermal radiation. As related to the human body, heat transfer includes the exchange of thermal energy between the body and the environment. In connection with a machine, heat transfer includes the exchange of thermal energy from within a machine to the environment or to another machine.

It is sometimes desirable to determine the thickness of a layer of a system, such as a machine or a body. For example, in the fields of medicine, health, and fitness it is desirable to calculate a thickness of a person's skin. A physician may require an estimation of the thickness of the patient's hypodermis at a particular region of the patient's body. Known methods, however, produce thickness estimations that are less accurate than desired. Accordingly, further advancements in the area of heat transfer and, more particularly, the estimation, detection, and calculation of a thickness of a layer are desirable.

SUMMARY

According to an exemplary embodiment of the disclosure, a thickness analyzer unit for determining a thickness of a layer includes a temperature change device, a temperature sensor, a memory, and a controller. The temperature change device is configured to induce a temperature change of the layer from a first temperature value at a first time to a second temperature value at a second time. The first temperature value is different from the second temperature value. The temperature sensor is configured to generate first temperature data corresponding to the first temperature value and second temperature data corresponding to the second temperature value. The memory is configured to store the first temperature value, the second temperature value, a thermal conductivity value of the layer, a specific thermal capacity value of the layer, and a density value of the layer. The controller is operatively connected to the temperature change device, the temperature sensor, and the memory. The controller is configured (i) to determine a time constant value of the layer based on the first temperature value and the second temperature value, and (ii) to determine the thickness of the layer based on the determined time constant, the thermal conductivity value, the specific thermal capacity value, and the density value. The thickness of the layer is stored in the memory as a thickness value.

According to another exemplary embodiment of the disclosure, a method for determining a thickness of a layer with a thickness analyzer unit, includes measuring a first temperature value of the layer with a temperature sensor of the thickness analyzer unit at a first time, inducing a temperature change of the layer with a temperature change device of the thickness analyzer unit, and measuring a second temperature value of the layer with the temperature sensor after inducing the temperature change at a second time. The method further includes determining a time constant value of the layer based on the measured first temperature value and the measured second temperature value with a controller of the thickness analyzer unit, storing a thermal conductivity value of the layer, a specific thermal capacity value of the layer, and a density value of the layer in a memory of the thickness analyzer unit, and determining a thickness value corresponding to the thickness of the layer based on the determined time constant value, the thermal conductivity value, the specific thermal capacity value, and the density value with the controller.

BRIEF DESCRIPTION OF THE FIGURES

The above-described features and advantages, as well as others, should become more readily apparent to those of ordinary skill in the art by reference to the following detailed description and the accompanying figures in which.

DETAILED DESCRIPTION

Figure 1:
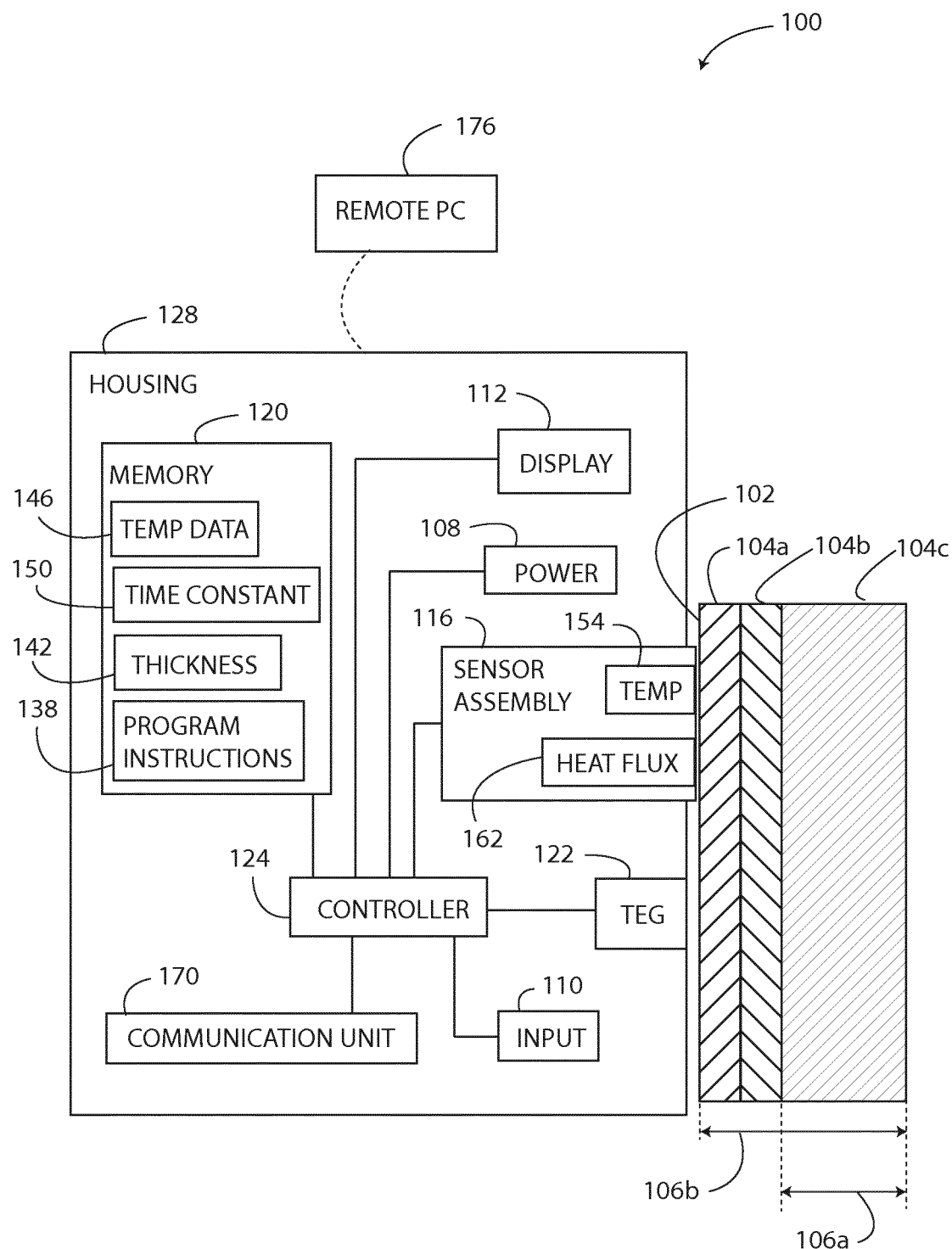
FIG. 1 is a block diagram of a thickness analyzer unit, as disclosed herein, that is configured to determine a thickness of a layer of a system.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

For the purposes of the disclosure, the phrase "A and/or B" means (A), (B), or (A and B). For the purposes of the disclosure, the phrase "A, B, and/or C" means (A), (B), (C), (A and B), (A and C), (B and C), or (A, B and C).

The terms "comprising," "including," "having," and the like, as used with respect to embodiments of the disclosure, are synonymous.

As shown in FIG. 1, a thickness analyzer unit 100 is configured to determine a thickness of a layer of any material by analyzing a thermal step response of the layer and determining a thermal time constant. The thickness of the layer is then calculated using the determined thermal time constant and at least one of a thermal conductivity value, a specific thermal capacity of the layer, and a density value of the layer. The method is applicable to systems such a machine or a human body. The calculation of the thickness of human skin (i.e. an exemplary layer) is used herein as an example only. The method is not limited to use with a human or animal system and may be used with any other system having layers.

The thickness analyzer unit 100 is placed against the skin 102 of a patient. The simplified skin 102 includes an epidermis layer 104a, a dermis layer 104b, and a hypodermis layer 104c (i.e. a fat layer). The epidermis layer 104a and the dermis layer 104b typically have about the same thickness at most of the locations on the body. Accordingly, an epidermis thickness of the epidermis layer 104a is a first constant value stored in the memory 120, and a dermis thickness of the dermis layer 104b is a second constant value stored in the memory 120. Moreover, the combined thickness of the epidermis layer 104a and the dermis layer 104b does not vary much from person to person. The hypodermis layer 104c, however, varies substantially from person to person and is also the thickest layer of the skin 102 at most locations of the body. A hypodermis thickness 106a of the hypodermis 104c depends on at least the selected body location, the gender, the weight, and the height of the person. Moreover, each of the epidermis layer 104a, the dermis layer 104b, and the hypodermis layer 104c are substantially continuous, meaning that there are no openings in the skin 102 by which the thickness of any of the layers 104a, 104b, 104c can be determined non-invasively, such as by a visual inspection. Accordingly, the dermis layer 104b completely covers the hypodermis layer 104c and the epidermis layer 104a completely covers the dermis layer 104b, such that the thickness of the layers 104a, 104b, 104c are completely obscured from view and cannot be determined without cutting the skin 102.

The analyzer unit 100 is configured to determine a combined thickness 106b of the skin 102 (or the thickness of a layer of any other material) based on a thermal step response of the skin 102 or the material layer being analyzed. The step response is a change in temperature of the skin 102 in response to a thermal input, such as the thermal output of the TEG 122. Specifically, in one embodiment, the analyzer unit 100 determines the combined thickness 106b of the epidermis 104a, the dermis 104b, and the hypodermis 104c, which is also referred to herein as a total thickness. Moreover, the analyzer unit 100 may use the determined combined thickness 106b to calculate material parameters of the skin 102 such as a heat transfer coefficient of the skin 102, a thermal resistance of the skin 102, and a thermal capacity of the skin 102. The analyzer unit 100 estimates the combined thickness 106b quickly, accurately, and non-invasively. The analyzer unit 100 accurately estimates and/or calculates the combined thickness 106b for all types of patients independent of gender, weight, height, and body mass index.

The thickness analyzer unit 100 includes a power supply 108, an input unit 110, a display 112, a sensor assembly 116, a memory unit 120, a thermoelectric generator 122, and a communication unit 170 operably connected to a controller 124. The power supply 108, the input unit 110, the display 112, the sensor assembly 116, the memory unit 120, the communication unit 170, and the controller 124 are each at least partially located within a housing 128. The housing 128 is configured to be gripped by a user during operation of the analyzer unit 100. The analyzer unit 100 is a handheld instrument that is lightweight, portable, and convenient to operate.

The power supply 108, in one embodiment, includes a battery. For example, the power supply 108 is a rechargeable lithium polymer battery. Accordingly, the analyzer unit 100 is cordless in use and does not require a wired connection to a mains power supply. In other embodiments, the power supply 108 is provided as any other power source (e.g. an energy harvester with a power management circuit).

The memory 120 of the analyzer unit 100 is an electronic data storage unit, which is also referred to herein as a non-transient computer readable medium. The memory 120 is configured to store program instruction data 138, layer thickness data 142, temperature data 146, time constant data 150, and other electronic data associated with operation of the analyzer unit 100.

The input unit 110 is configured to receive input data via manipulation by a user. The input unit 110 may be configured as a touchscreen applied over the display 112 that is configured to enable a user to input data via the touch of a finger and/or a stylus. In another embodiment, the input unit 110 comprises any device configured to receive user inputs, as may be utilized by those of ordinary skill in the art, including e.g., one or more buttons, switches, keys, and/or the like.

The display 112 is configured to display a visual representation of at least the thickness data 142. The display 112 may comprise a liquid crystal display (LCD) panel configured to display static and dynamic text, images, and other visually comprehensible data. The display 112, in another embodiment, is any display unit as desired by those of ordinary skill in the art.

The thermoelectric generator 122, which is also referred to herein as a temperature change device and a heating/cooling thermoelectric generator ("TEG"), is configured to induce a temperature change of the layer by exhibiting a thermal output. For example, the TEG 122 is configured to heat or to cool the skin 102 or the layer to be measured for thickness. In such an embodiment, the TEG 122 may be applied directly to the skin 102 to induce a temperature change with the thermal output. Moreover, the TEG 122 may also be configured to heat/cool the ambient environment around the skin 102 using the thermal output, but without contacting the skin 102. In one embodiment, the ambient environment includes at least the environment surrounding the TEG 122, the housing 128, the air near the TEG 122, and/or clothing near the TEG 122. In the case of a human or animal patient, the TEG 122 warms/cools the skin 102 with the thermal output but does not burn or otherwise harm the patient. In another embodiment, the TEG 122 is a separate instrument from the analyzer unit 100. Moreover, in some embodiments, the TEG 122 is configured to measure heat flux of the skin 102 and to generate heat flux data, which is stored in the memory 120.

The controller 124 of the analyzer unit 100 is configured to execute the program instruction data 138 for controlling the sensor assembly 116 and determining/calculating the combined thickness 106b of the skin 102, which is stored as a thickness value of the thickness data 142 in the memory 120. The controller 124 is provided as a microprocessor, a processor, or any other type of electronic control chip.

The sensor assembly 116 includes a temperature sensor 154 and a heat flux sensor 162. The temperature sensor 154 is configured to measure a temperature of the layer to be measured for thickness and to generate corresponding temperature data 146. In the exemplary embodiment, the temperature sensor 154 measures a temperature of the surface of the patient's skin 102. The temperature sensor 154 is typically configured for placement directly against the skin 102. The temperature sensor 154 generates an electrical temperature output signal based on the sensed temperature. The electrical temperature output signal is received by the controller 124 and includes the temperature data 146.

The heat flux sensor 162 is configured to measure heat flux at the surface of the layer to be measured for thickness. In the exemplary embodiment, the heat flux sensor 162 measures the heat flux at the surface of the patient's skin 102. The heat flux sensor 162 is typically configured for placement directly against the skin 102. In one embodiment, "heat flux" corresponds to a measured heat rate divided by a surface area of the heat flux sensor 162. In the case of a human or an animal, heat rate corresponds to the rate at which the body radiates or loses heat. The heat flux sensor 162 generates an electrical flux output signal based on the sensed heat flux. The electrical flux output signal is received by the controller 124 and includes the heat flux data.

The communication unit 170 is a wireless or wired data transceiver unit that is configured to transmit data to an end device 176 and to receive data from the end device 176. For example, the communication unit 170 is configured to transmit at least some of the electronic data stored in the memory 120 (i.e. the computed results, such as the thickness value of the thickness data 142) to the end device 176, which is provided as a smartphone or a PC. In some embodiments, instead of the controller 124 generating the thickness data 142, the end device 176 generates the thickness data 142 and transmits the thickness data 142 to the analyzer unit 100. In such an embodiment, the communication unit 170 receives the thickness data 142 from the end device 176. In a further embodiment, the thickness data 142 is generated in the cloud, transmitted to the analyzer unit 100, and received by the communication unit 170.

Figure 2:
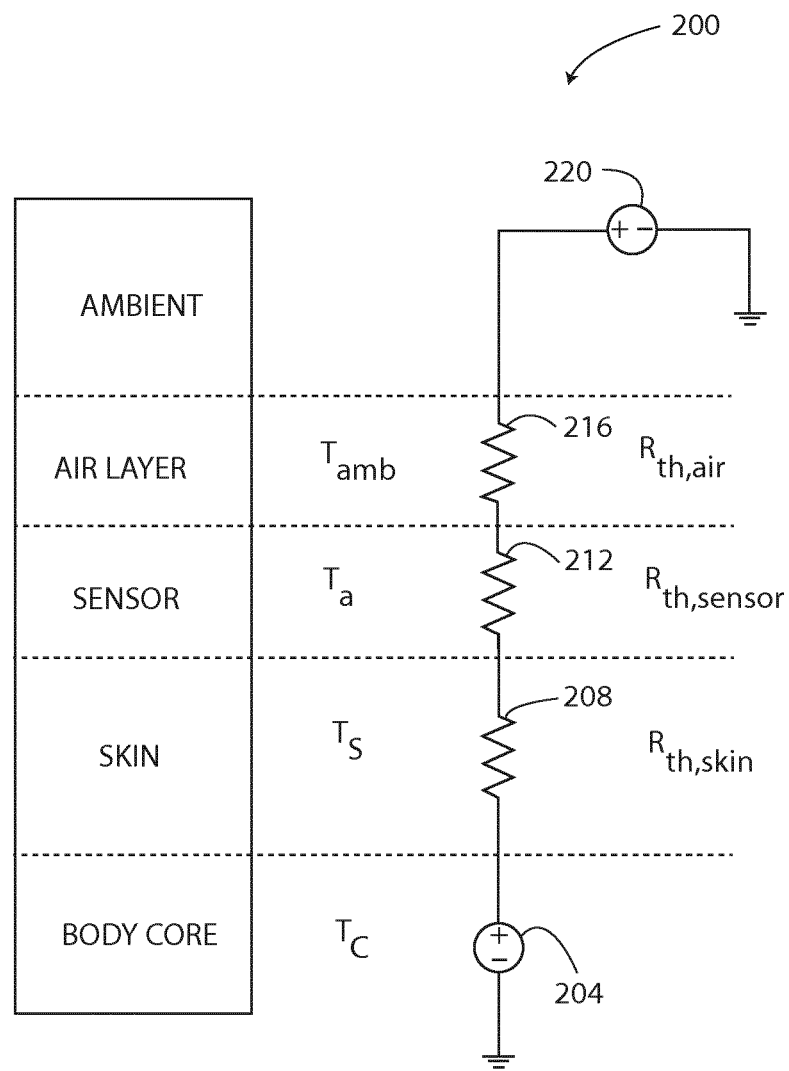
FIG. 2 is a diagram and a schematic of an electrical model of heat transfer through an exemplary system shown as a human body.

With reference to FIG. 2, in one embodiment, heat transfer through the human body is based on an electrical circuit model 200 of a first order system. The model 200 includes a voltage source 204 electrically connected to a series connection of a skin resistor 208, a sensor resistor 212, an air resistor 216, and another voltage source 220. The voltage source 204 models the patient's body core temperature and the magnitude of the voltage of the voltage source 204 corresponds to the temperature generation/output of the patient's body. In one embodiment, the magnitude of the voltage source 204 corresponds to the patient's core body temperature.

The skin resistor 208 exhibits an electrical resistance that corresponds to a thermal resistance of the patient's skin 102. The skin thermal resistance is a resistance of the patient's skin 102 to changes in temperature. The electrical resistance of the skin resistor 208 is based on a total thermal resistance of each layer of the patient's skin 102 including the epidermis 104a, the dermis 104b, and the hypodermis 104c.

The sensor resistor 212 exhibits an electrical resistance that corresponds to a thermal resistance of the sensor assembly 116 to changes in temperature. The thermal resistance of the sensor assembly 116 is a resistance of the sensor assembly 116 to changes in temperature.

The air resistor 216 exhibits an electrical resistance that corresponds to a thermal resistance of the air adjacent to the patient's skin 102. The air thermal resistance is a resistance of the air around the patient and the analyzer unit 100 to changes in temperature.

The magnitude of the voltage source 220 corresponds to the temperature generation/output of the ambient area/environment surrounding the patient. The voltage sources 204, 220 oppose each other, such that voltage from the voltage source 204 opposes voltage from the voltage source 220.

The model 200 approximates heat flow through the skin 102 accounting for three thermal resistances modeled by the skin resistor 208, the sensor resistor 212, and the air resistor 216. In one embodiment, the model 200 is illustrated as a static model that does not account for thermal capacities of the layers 104a, 104b, 104c of the skin 102. The model 200 is configurable to account for dynamic behavior by modeling the thermal capacity of at least the hypodermis 104c.

As shown the following chart, for each electrical variable of the model 200 there is a corresponding thermal variable corresponding to the patient and/or the patient's environment.

| Thermal | | | Electrical | | |
|---|---|---|---|---|---|
| Variable | Symbol | Unit | Variable | Symbol | Unit |
| Temperature | T | K | Voltage | V | V |
| Heat Transfer Rate | q | W | Current | I | A |
| Heat Flux | Q″ | W/m² | Current density | J | A/m² |
| Thermal Resistance | $R_{th}$ | K/W | Resistance | R | Ω |
| Thermal Capacity | $C_{th}$ | Ws/K | Capacitance | C | As/V |

According to the chart, temperature ("T") corresponds to voltage ("V"), heat transfer rate ("q") corresponds to electrical current ("I"), heat flux ("Q‴") corresponds to electrical current density ("J"), thermal resistance ("$R_{th}$") corresponds to electrical resistance ("R"), and thermal capacity ("$C_{th}$") corresponds to electrical capacity ("C"). The electrical model 200 and the thermal equivalents are manipulated below in order to determine a thermal time constant value ("τ") of the skin 102 or the layer to be measured for thickness. The thermal time constant value ("τ") is used with at least one of a thermal conductivity value ("k"), a specific thermal capacity value ("$c_p$"), and a density value ("ρ") of the skin 102 to calculate the combined thickness 106b (i.e. a thickness value of the thickness data 142) with the controller 124. In an embodiment, the thermal conductivity value ("k"), the specific thermal capacity value ("$c_p$"), and the density value ("ρ") of the skin 102 are assumed to have constant values for all patients, since the composition of the skin 102 is substantially the same across all patients. The thermal time constant value ("τ") is based on the time required to heat or cool a material by 63.2% from an initial temperature to a different temperature. The percentage is an approximation defined as (1−e⁻¹), where ("e") is Euler's number, which is a constant.

Based on the above chart and model, Ohm's law is written using the corresponding thermal variables. To begin, using electrical variables, Ohm's law solved for electrical current can be written as equation (1).

$$I = \frac{\Delta V}{R} \quad (1)$$

Replacing the electrical variables in equation (1) with the corresponding thermal variables from the chart yields equation (2), which determines the heat transfer rate.

$$q = \frac{\Delta T}{R_{th}} \quad (2)$$

Moreover, electrical current density is written as shown in equation (3).

$$J = \frac{\Delta V}{R \cdot \text{Area}} \quad (3)$$

Replacing the electrical variables in equation (3) with the corresponding thermal variables yields equation (4), which is an equation used to determine heat flux in a thermal system, since in the model 200 electrical current density corresponds to the heat flux. The Area variable is a surface area and is the same in both the electrical variables and the thermal variables. Typically, the Area variable corresponds to a surface area of the area being measured for thickness/temperature. Also, the Area may be the area sensed by the heat flux sensor 162.

$$\dot{Q}'' = \frac{\Delta T}{R_{th} \cdot \text{Area}} \quad (4)$$

For each material layer (i.e. layers 104a, 104b, 104c of the skin 102, for example) a thermal resistance can be calculated with equation (5a).

$$R_{th} = \frac{\Delta x}{k \cdot \text{Area}} = \frac{1}{h \cdot \text{Area}} \quad (5a)$$

In equation (5a), $\Delta x$ corresponds to a thickness value of the thickness data 142 of the material layer and k corresponds to a thermal conductivity value of the layer.

The thermal capacity of each material layer (i.e. layers 104a, 104b, 104c of the skin 102, for example) can be calculated with equation (5b).

$$C_{th} = c_p \cdot \rho \cdot \Delta x \cdot A \quad (5b)$$

In equation (5b), $c_p$ corresponds to specific thermal capacity value and $\rho$ corresponds to a density value of the layer.

The heat flux sensor 162 is configured to measure the heat flux $\dot{Q}''$ through the sensor assembly 116 at the surface of the skin 102 (or the surface of the layer to be measured for thickness). In one embodiment, a simplification is made that the heat flow through the skin 102 and the sensor assembly 116 is only perpendicular to the skin layer 102, and that the heat flux through the skin 102 equals the heat flux through the heat flux sensor 162. Based on the above, a temperature difference (i.e. a change in temperature) across the skin 102 is modeled by equation (6).

$$\Delta T = T_C - T_S \quad (6)$$

In equation (6), $\Delta T$ is the change in temperature between two physical locations at the same instance in time, Tc is the core body temperature, and Ts is the surface temperature of the skin 102. Core body temperature is the temperature of the internal environment of the body of the patient. A normal core body temperature of a human is about 37° C. Typically, the core body temperature is greater than the surface temperature of the skin 102. The core body temperature can be calculated with the following equation (7).

$$T_C = \frac{\dot{Q}''}{h_S} + T_S \quad (7)$$

In equation (7), the change in temperature $\Delta T$ has been replaced with the heat flux through the sensor assembly 116 (i.e. $\dot{Q}''$) divided by a heat transfer coefficient of the skin ("$h_s$"). The heat transfer coefficient of the skin ($h_s$) depends on the thermal conductivity of the skin 102 (i.e. one over the thermal resistance of the skin 102) and the area through which the heat flux is measured (i.e. the Area). Based on the model 200 and various other equations set forth below, the time constant value ("$\tau$") of the skin 102 can be determined, which is used to calculate the combined thickness 106b.

Figure 3:
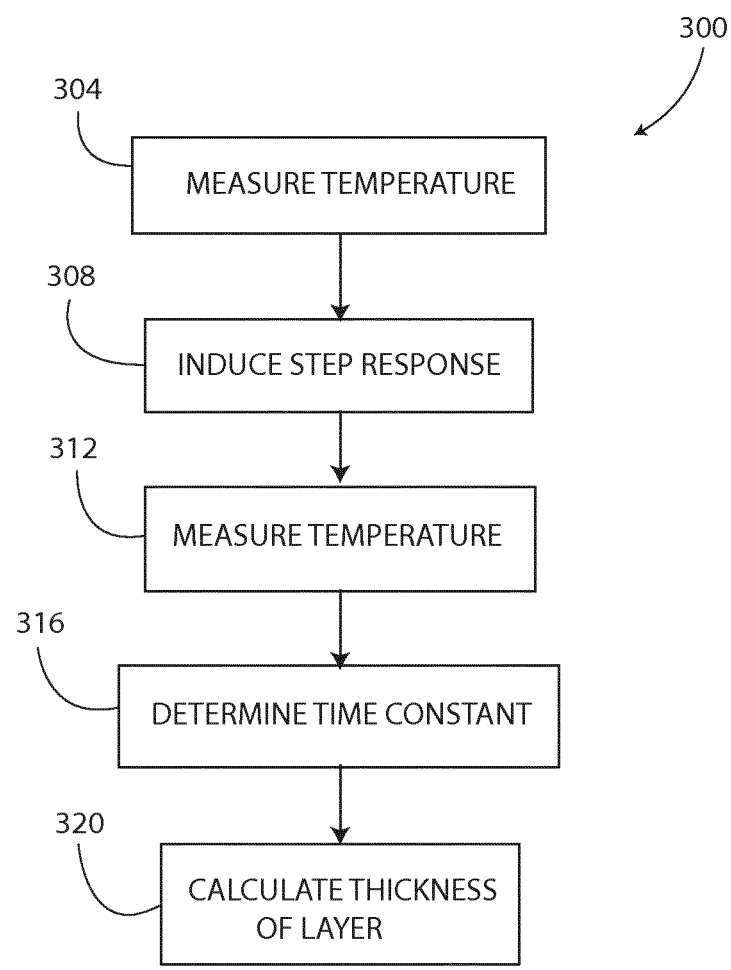
FIG. 3 is a flowchart illustrating an exemplary method for operating the analyzer unit of FIG. 1.

In operation, the analyzer unit 100 estimates/calculates the thickness value of a layer of a system according to a method 300 illustrated by the flowchart of FIG. 3. As set forth below, the analyzer unit 100 determines and analyses a thermal step response of the skin 102 based on the electrical model 200 of heat transfer through the human body.

As shown in block 304, the analyzer unit 100 measures a surface temperature of the layer to be measured for thickness. In particular, the analyzer unit 100 uses the temperature sensor 154 to measure a surface temperature of the skin 102. The measured surface temperature of the skin 102 is stored in the memory 120 as the temperature data 146 and is referred to herein as either a start temperature $T_1$, a first temperature value at a first time, or a first temperature data stored in the memory 120.

Next in block 308, the analyzer unit 100 induces a step response in the skin 102 or the material to be measured for thickness. In one embodiment, the TEG 122 is used to induce the temperature change of the layer by warming or cooling the skin 102, thereby causing the skin 102 to change from the start temperature $T_1$ to a settled temperature $T_2$ (i.e. a second temperature value at a second time). In another embodiment, the step response is caused by changing the ambient temperature of the air surrounding the skin 102 if the skin 102 is exposed to the surrounding air. These methods are suitable for inducing the step response of any object where the core temperature is substantially constant, such as the human body. A "substantially constant" core temperature is a core temperature having a thermal time constant that is at least twenty times greater than the thermal time constant of the layer being measured. The step response can also be externally applied, e.g. with a heating/cooling element.

Following inducement of the step response, in block 312 the analyzer unit 100 uses the temperature sensor 154 to make a series of temperature measurements in order to determine the step response. In one embodiment, the analyzer unit 100 measures again the surface temperature of the skin 102 (at least once and typically numerous times) after the step response. The measured surface temperature of the skin 102 after the step response is stored in the memory 120 as the temperature data 146 and is referred to herein as either a settled temperature $T_2$, a second temperature value, or as second temperature data stored in the memory 120 as the temperature data 146. The settled temperature $T_2$ is different from the start temperature $T_1$.

The step response of the electrical model 200 of FIG. 2 is described with an exponential function. As applied to a corresponding thermal system, such as the skin 102, the temperature of the skin 102 is described by the following equation (8).

$$T = T_1 + dT * \left(1 - e^{-\frac{t}{\tau}}\right) \quad (8)$$

In equation (8), T is the temperature as dependent on time, t is the time, $T_1$ is the start temperature, $T_2$ is the settled temperature, and dT is a temperature difference equal to $T_2 - T_1$.

Figure 4:
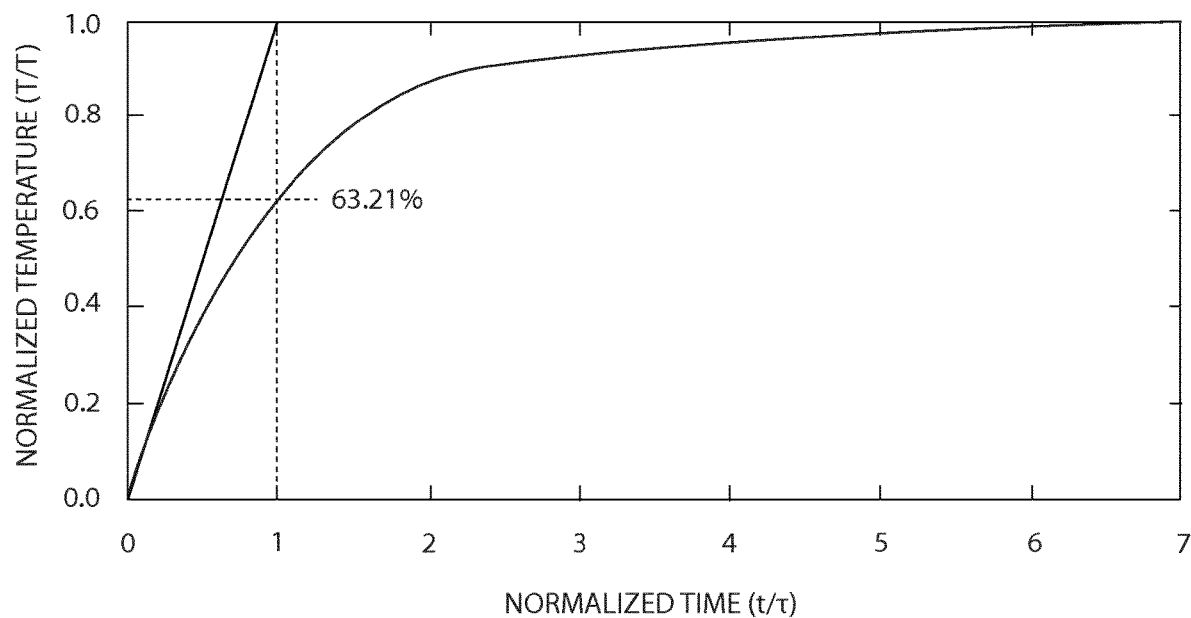
FIG. 4 is a graph of normalized temperature versus normalized time.

FIG. 4 illustrates a temperature measurement of the skin 102 in response to the step response. In FIG. 4, the time axis is normalized over the time constant τ. The temperature axis is normalized over the settled temperature $T_2$ and the start temperature $T_1$ equals 0.

In block 316, the analyzer unit 100 determines the thermal time constant value ("τ") of the thermal system (e.g. the skin 102) and stores the time constant value as the time constant data 150 in the memory 120. Corresponding to an electrical system, the thermal time constant value ("τ") of a dynamic system can be determined by measuring the temperature step response in response to a quick temperature change. Since, in this example, only one skin layer is considered (e.g. the combined thickness 106b), the skin 102 is approximated as a first order system with one thermal resistance and one specific thermal capacity for the skin 102.

Since the skin 102 is modeled to have only one layer, the thermal time constant can be calculated by the following equation (9).

$$\tau = R_{th} \cdot C_{th} \qquad (9)$$

The variables in equation (9) are described above in equations (5a) and (5b). Performing the appropriate substitution in equation (9) yields the following equation (10) representing the time constant.

$$\tau = \frac{1}{k} \cdot (\Delta x)^2 \cdot c_p \cdot \rho \qquad (10)$$

In practice, equation (10) provides at least two methods for determining the time constant value using the controller 124 of the analyzer unit 100. In both of the methods the step response is known including the start temperature $T_1$ and the settled temperature $T_2$. In a first method for determining the time constant, after a predetermined time period equal to the time constant (i.e. (t=τ)), the temperature of the system is 63.2% from the start temperature $T_1$ to the settled temperature $T_2$ (see FIG. 4). Thus, the time constant value is simply read from a plot of the temperature data. Accordingly, with the start temperature $T_1$ and the settled temperature $T_2$ known, the temperature of the skin 102 which is 63.2% from the start temperature $T_1$ to the settled temperature $T_2$ can be calculated as follows from equation (11).

$$T_{63.2\%} = T_1 + 0.632 \cdot (T_2 - T_1) \qquad (11)$$

In a second method for determining the time constant after the predetermined time period in which t=τ, a tangent of the temperature step response at t=0 reaches the value of the settled temperature $T_2$, as shown in FIG. 4. Therefore, the slope of the tangent m multiplied by the time constant value equals the steady state value of the temperature. Accordingly, using this method the time constant value can be calculated as follows from equation (12).

$$\tau = \frac{T_2}{m} \qquad (12)$$

Another method to calculate the time constant value uses an exponential function, which describes the temperature step response of the skin 102. One point on the step response ($t_x$, $T_x$) before the graph starts to settle, is known. The exponential function is shown below as equation (13).

$$T_x = T_1 + dT * \left(1 - e^{-\frac{t_x}{\tau}}\right) \qquad (13)$$

In this method, the analyzer unit 100 determines the values $t_x$, $T_x$, the start temperature $T_1$, and the temperature difference dT, and calculates the time constant according to equation (14).

$$\tau = \frac{-t_x}{\ln\left(1 - \frac{T_x - T_1}{dT}\right)} \qquad (14)$$

In yet another embodiment, the time constant value is generated based at least in part on the measured heat flux as determined by the heat flux sensor 162 (i.e. the heat flux data).

With reference again to FIG. 3, after determining the time constant value with the controller 124, in block 320 the analyzer unit 100 calculates the combined thickness 106b of the skin 102 or the material to be measured. Specifically, the analyzer unit 100 calculates the combined thickness 106b using equation (15), which is based on the determined time constant ("τ"), the thermal conductivity value ("k"), the specific thermal capacity value ("$c_p$"), and the density value ("ρ").

$$\Delta x = \sqrt{\frac{\tau \cdot k}{c_p \cdot \rho}} \qquad (15)$$

After calculating the combined thickness 106b, the combined thickness 106b is stored in the memory 120 as the thickness data 150. In one embodiment, the thickness data 150 is stored as data corresponding to a thickness of the combined thickness 106b in millimeters, for example. An exemplary combined thickness 106b is ten millimeters (10 mm). In another embodiment, the thickness data 150 is stored as a proportional representation of the combined thickness 106b. For example, a thickness value of the combined thickness 106b is a number from zero to 255, with zero corresponding to zero millimeters and 255 corresponding to ten millimeters (10 mm). Any other proportional representation may be used for the thickness data 150 depending on the embodiment.

In another embodiment, the system (e.g. the human body) is modeled as a $3^{rd}$ order system instead of a $1^{st}$ order system. In such an embodiment, the skin 102 may be modeled using a thermal resistance value and a thermal capacity value for each of the three skin layers 104a, 104b, 104c. Since the epidermis 104a and the dermis 104b are mostly constant in thickness across humans, these constant thicknesses are subtracted from the combined thickness 106b to calculate the hypodermis thickness value 106a.

Figure 5:
FIG. 5 is block diagram illustrating a transfer function.

With reference to FIG. 5, in another embodiment, the combined thickness 106b is determined without inducing the temperature step response. For example, one approach is to apply a known arbitrary temperature progression, while the surface temperature of the skin 102 is measured by the temperature sensor 154. The arbitrary temperature can be applied directly or indirectly. Moreover, the arbitrary temperature progression can be a passive temperature progression. That is, a change in the ambient temperature, which is measured. In such an embodiment, a corresponding transfer function may be described with an exponential function or functions of higher order systems. Since the transfer function with the input temperature (i.e. the ambient temperature) and the output temperature (i.e. the surface temperature) are known, the thermal time constant can be determined. In this embodiment, the input temperature progression changes fast enough to allow the determination of the time constant. Thus, in this embodiment, the input temperature equals a change in the ambient temperature, and the output temperature equals the surface temperature.

The analyzer unit 100 may use the determined combined thickness 106*b* and the thermal conductivity value ("k") to determine the heat transfer coefficient of the skin 102 ("h") according to equation (16). Thereafter, the analyzer unit 100 may calculate the core body temperature using at least the heat transfer coefficient of the skin.

$$h = \frac{k}{\Delta x} \quad (16)$$

As noted throughout this disclosure, the methods, embodiments, and concepts are not only applicable to determining the thickness of the skin 102, but also the thickness of a layer of any material. This includes layers that are substantially continuous and for which the thickness cannot be determined by visual inspection. To this end, the temperature sensor 154 of the analyzer unit 100, which measures surface temperature, is selected to have a faster time response (i.e. a first time response) in response to the thermal output of the TEG 122 than a second time response of the material(s) to be measured in response to the thermal output, such that the analyzer unit 100 may monitor the induced temperature step response. Typically, the material to be measured has a comparatively small thickness against the surface area, so it is considered as a layer. When this condition is met, the assumption that heat transfer is only perpendicular to the area of the material is met.

The analyzer unit 100 is an improvement to computer functionality because, as compared to prior devices, the analyzer unit 100 determines the thickness of a layer more quickly, more accurately, and with a less complicated processing approach. Some prior devices use an ultrasound approach, for example, that is expensive and complicated to operate. Moreover, ultrasound thickness measuring devices are limited to only certain types of systems. Whereas, in comparison, the analyzer unit 100 is simple and fast to operate and can determine the thickness of any layer that is part of a system that exhibits a substantially constant core temperature. Other prior thickness measuring devices use a resonant frequency approach and must be placed on a suitably flat metal surface and, therefore, cannot be used to measure the thickness of a biological layer, such as the skin 102.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A thickness analyzer unit for determining a thickness of a layer, comprising:
   a temperature change device configured to induce a temperature change of the layer from a first temperature value at a first time to a second temperature value at a second time, the first temperature value different from the second temperature value;
   a temperature sensor configured to generate first temperature data corresponding to the first temperature value and second temperature data corresponding to the second temperature value;
   a heat flux sensor configured to directly measure a heat flux at a surface of the layer and to generate corresponding heat flux data;
   a memory configured to store the first temperature value, the second temperature value, the heat flux data, a thermal conductivity value of the layer, a specific thermal capacity value of the layer, and a density value of the layer; and
   a controller operatively connected to the temperature change device, the temperature sensor, the heat flux sensor, and the memory, the controller configured (i) to determine a time constant value of the layer based on the first temperature value and the second temperature value, and (ii) to determine the thickness of the layer based on the determined time constant value, the heat flux data, the thermal conductivity value, the specific thermal capacity value, and the density value,
   wherein the thickness of the layer is stored in the memory as a thickness value,
   wherein the temperature change device defines a surface configured to be applied directly to the surface of the layer to induce the temperature change,
   wherein the heat flux sensor defines a surface configured to be applied directly to the surface of the layer to directly measure the heat flux,
   wherein the layer is human skin,
   wherein the human skin includes an epidermis layer, a dermis layer, and a hypodermis layer,
   wherein an epidermis thickness of the epidermis layer is a first constant value stored in the memory,
   wherein a dermis thickness of the dermis layer is a second constant value stored in the memory,
   wherein the controller is further configured to determine a hypodermis thickness value of the hypodermis layer by subtracting the first constant and the second constant from the thickness value, and
   wherein the hypodermis thickness value is stored in the memory.

2. The thickness analyzer unit of claim 1, wherein the temperature change device is a thermoelectric generator configured to heat the layer to induce the temperature change.

3. The thickness analyzer unit of claim 1, wherein the temperature change device is a thermoelectric generator configured to cool the layer to induce the temperature change.

4. The thickness analyzer unit of claim 1, wherein:
   the temperature change device exhibits a thermal output that changes the temperature of the layer to induce the temperature change,
   the temperature sensor has a first time response in response to the thermal output,
   the layer has a second time response in response to the thermal output, and the first time response is less than the second time response.

5. The thickness analyzer unit of claim 1, wherein the time constant value corresponds to a time required to change a temperature of the layer by 63.2% of an initial temperature value.

6. The thickness analyzer unit of claim 1, wherein the layer is substantially continuous and the thickness of the layer cannot be determined by a visual inspection.

7. The thickness analyzer unit of claim 1, wherein:
the controller is configured to determine the thickness value according to the following relationship $$\Delta x = \sqrt{\frac{\tau \cdot k}{c_p \cdot \rho}}$$

$\Delta x$ corresponds to the thickness value,
$\tau$ corresponds to the time constant value,
k corresponds to the thermal conductivity value,
$c_p$ corresponds to the specific thermal capacity, and
$\rho$ corresponds to the density value.

8. A method for determining a thickness of a layer with a thickness analyzer unit, comprising:
measuring a first temperature value of the layer with a temperature sensor of the thickness analyzer unit at a first time;
inducing a temperature change of the layer with a temperature change device of the thickness analyzer unit;
measuring a second temperature value of the layer with the temperature sensor after inducing the temperature change at a second time;
directly measuring a heat flux of a surface of the layer with a heat flux sensor of the thickness analyzer unit and generating corresponding heat flux data with a controller of the thickness analyzer unit;
determining a time constant value of the layer based on the measured first temperature value and the measured second temperature value with the controller of the thickness analyzer unit;
storing a thermal conductivity value of the layer, a specific thermal capacity value of the layer, and a density value of the layer in a memory of the thickness analyzer unit; and
determining a thickness value corresponding to the thickness of the layer based on the determined time constant value, the heat flux data, the thermal conductivity value, the specific thermal capacity value, and the density value with the controller,
wherein inducing the temperature change of the layer comprises heating the layer with a surface of the temperature change device of the thickness analyzer unit applied directly to the surface of the layer,
wherein directly measuring the heat flux comprises applying a surface of the heat flux sensor directly to the surface of the layer,
wherein the layer is human skin,
wherein the human skin includes an epidermis layer, a dermis layer, and a hypodermis layer, and
wherein the method further comprises:
storing a first constant value corresponding to a thickness of the epidermis layer in the memory;
storing a second constant value corresponding to a thickness of the dermis layer in the memory;
determining a hypodermis thickness value corresponding to a thickness of the hypodermis layer by subtracting the first constant and the second constant from the thickness value with the controller; and
storing the hypodermis thickness value in the memory.

9. The method as claimed in claim 8, wherein inducing the temperature change of the layer comprises:
cooling the layer with the temperature change device of the thickness analyzer unit applied directly to the layer.

10. The method as claimed in claim 8, wherein the layer is substantially continuous and the thickness of the layer cannot be determined by a visual inspection.

11. The method as claimed in claim 8, wherein:
the controller is configured to determine the thickness value according to the following relationship $$\Delta x = \sqrt{\frac{\tau \cdot k}{c_p \cdot \rho}}$$

$\Delta x$ corresponds to the thickness value,
$\tau$ corresponds to the time constant value,
k corresponds to the thermal conductivity value,
$c_p$ corresponds to the specific thermal capacity, and
$\rho$ corresponds to the density value.

12. The thickness analyzer unit of claim 1, wherein the controller is configured to determine the time constant value of the layer based on the first temperature value, the second temperature value, and the heat flux data.

13. The thickness analyzer unit of claim 1, wherein a thermoelectric generator is configured as the temperature change device and the heat flux sensor.

14. The method as claimed in claim 8, wherein the time constant value is determined based on the first temperature value, the second temperature value, and the heat flux data.

* * * * *